United States Patent [19]

Rothermel

[11] 4,237,652
[45] Dec. 9, 1980

[54] METHOD OF BREEDING AND PRODUCING SEED CORN

[76] Inventor: Alan F. Rothermel, P.O. Box 79, West Liberty, Iowa 52776

[21] Appl. No.: 118,588

[22] Filed: Feb. 4, 1980

Related U.S. Application Data

[63] Continuation-in-part of Ser. No. 917,966, Jun. 22, 1978, abandoned.

[51] Int. Cl.³ ............................................. A01H 1/02
[52] U.S. Cl. ................................... 47/58; 47/DIG. 1
[58] Field of Search ............................ 47/58, DIG. 1

[56] References Cited

U.S. PATENT DOCUMENTS 2,753,663  7/1956  Jones ........................................ 47/58
4,051,629  10/1977  Galinat ..................................... 47/58

OTHER PUBLICATIONS

Effect of non-pollination . . . , Russell et al., Crop Science, vol. 16, #2, Mar.-Apr. 1976.

Primary Examiner—Robert E. Bagwill
Attorney, Agent, or Firm—James C. Nemmers; Haven E. Simmons

[57] ABSTRACT

A method of breeding yellow dent hybrid seed corn by causing pollination of the silks of an ear other than the top ear of the corn plant with the resulting fertilization of the lower ear. The method is accomplished by causing the ear shoot at the top of the plant to abort before the silks emerge from that shoot, and then allowing a lower ear to produce silks and receive pollen from the male seed parent. Fertilization of the second or lower ear is then accomplished resulting in a corn plant that provides seed ($F_1$) which will in turn produce a higher yield in the farmer's field. (F is the designation of generations of plants, $F_1$ being the first filial generation.)

7 Claims, No Drawings

METHOD OF BREEDING AND PRODUCING SEED CORN

This application is a continuation-in-part of my co-pending application Ser. No. 917,966 filed June 22, 1978 and now abandoned.

BACKGROUND OF THE INVENTION

In the agricultural industry, research is continuously being conducted in order to improve the quality of the food produced and the productivity of the food producer or farmer. The production of corn is no exception, and there have been developed over the years methods and techniques for increasing the productivity of the farmer so that the farmer can produce higher yields. See Poehlman, John Milton: "Breeding Field Crops" Henry Holt & Company, Inc., 1959, pp. 241–277. Crops such as corn can be planted in higher densities to increase the farmer's per acre yield. However, there are obvious practical limits on such high density crop production. Moreover, crops such as corn which are planted in high density fields are more subject to stress from weather and more susceptible to disease. There have been developed breeding techniques for corn production, some of which have improved the farmer's yield. Examples of such breeding techniques are disclosed in U.S. Pat. No. 2,753,663 entitled "Production of Hybrid Seed Corn", U.S. Pat. No. 3,710,511 entitled "Procedures for Use of Genic Male Sterility and Production of Commercial Hybrid Maize", and in U.S. Pat. No. 4,051,629 entitled "Hybrid Seed Production".

The methods and techniques described in U.S. Pat. No. 2,753,663 were extensively used commercially and were quite successful until it was learned that the corn plants produced using such methods and techniques were susceptible to corn blight which could in a single season substantially destroy a farmer's crop. There is therefore a need for breeding and production techniques which will produce yield increases without affecting the quality of the corn produced or without rendering the corn more susceptible to the stresses of weather and disease.

In 1976, C. L. Prior and W. A. Russell published the results of their studies comparing the yields of first and second ears where pollination was prevented on one of the ears. Russell, W. A. and Prior, C. L., Crop Science, Vol. 16, No. 2, March-April 1976. "Effect of Non Pollination of First or Second Ears of Non Prolific and Prolific Maize Hybrids". Their results show that the second ear yields less than the first ear. These studies were, however, concerned only with one generation of seed. The method of the invention goes into another generation—the grow-out of the seed produced from the top ear and the lower ear. It is therefore the principal object of the invention to increase the farmer's yield substantially by use of a seed corn produced according to a method and technique that is not only novel but contrary to the teachings of the prior art.

SUMMARY OF THE INVENTION

According to the invention, techniques are employed whereby an ear on the corn plant other than the top ear is selected for fertilization. In order to achieve fertilization of a second or lower ear, fertilization of the top ear shoot is prevented, and thus abortion of the lower ears does not occur allowing a lower ear to receive pollen from the male seed parent. The seed corn thus produced by fertilizing a lower ear will when planted produce a substantially higher yield. My research indicates improved yields up to 25% over the conventional methods of breeding and producing yellow dent seed corn.

DESCRIPTION OF THE PREFERRED EMBODIMENT OF THE INVENTION

As is well known to those skilled in the art, in all known seed corn breeding techniques, regardless of whether used on single, three-way, double or other cross corn, the top ear is pollinated and fertilized to produce the mature grain. The particular genetic code produced using known breeding and production techniques, is dried, conditioned, and used by the farmer as seed corn. As is well known in the production of seed corn, there are a variety of preferred inbreds that are commercially used, these inbreds being crossed in various combinations to produce different varieties of seed corn ($F_1$) that are planted by the farmer. (F is the designation of generations of plants, $F_1$ being the first filial generation.)

In seed corn production, the top ear of each plant is used for pollinating and fertilization because it is the top ear shoot from which the silks first emerge. If these silks receive pollen from the male seed parent and the ear thus becomes fertilized, the lower one or two ear shoots will almost always naturally abort. Thus, the top ear on the corn plant is the only one which normally becomes fertilized and produces seed corn.

This is also true in commercial corn production of the corn belt varieties. If the top ear shoot becomes fertilized, the next lower one or two ear shoots will almost always naturally abort. There are southern corn belt varieties which when planted in low populations of 8,000 to 10,000 plants per acre usually will produce more than one ear per stalk. Russell, W. A., and Hallauer, A. R., 1968 Iowa Farm Science, Vol. 23, No. 3, pp 3-7, "Multiple Eared Corn May Give Farms More Stable Yields." However, in commercial corn production, populations of 18,000 to 30,000 plants per acre are almost always used in the U.S. North Central corn belt, and with such commercial populations, all corn belt varieties will almost always produce only a single ear. Southern corn varieties planted at the lower populations usually produce more than one ear per stalk because of the "plant density effect". However, if these southern corn varieties are planted at the higher densities, this prolific effect is usually masked.

My novel method of producing seed corn requires pollinating and fertilizing one of the ears below the top ear. Since the lower ears naturally abort after the top ear is pollinated, it is necessary to prevent the top ear from being fertilized. This is preferably accomplished by physically removing the top ear shoot before the silks emerge, but any other technique may be used that will produce abortion or nonpollination of the top shoot. Normally, there is a very short period (approximately 48 hours) after the ear shoot appears and before the silks emerge. It is during this short period that the top ear shoot can be aborted or covered with a shoot bag. If the top ear shoot is not fertilized or is aborted, the next lower ear will not abort and silks will emerge from the lower ear. The $F_1$ seed saved from the lower ear, rather than top ear, results in a hybrid which when planted will produce a higher yield. My research indicates up to 25% higher yields using seed produced from this novel method.

For my experiments, I used seven commercial single crosses, which I classified into three Types: Type 1, pure-line single crosses; Type2, closely related sister-line single crosses; and Type 3, widely modified single-crosses or three-way crosses. Pedigrees are listed in the following Table 1. To produce seed from the lower ear, the top ear shoots were physically removed before the silks emerged. Seed from the top ear was produced in a conventional manner.

TABLE 1

Pedigrees for the seven hybrids, classified into three types.

TYPE 1: PURE-LINE SINGLE CROSS

| Type | Pedigree |
|---|---|
| Type 1-A | B73 × MO17 |
| Type 1-B | B73Ht × W64A |
| Type 1-C | MO17 × N28 |

TYPE 2: CLOSELY RELATED SISTER-LINE SINGLE CROSS

| Type | Pedigree |
|---|---|
| Type 2-A | (A632Ht × A634Ht) × H99 |
| Type 2-B | (A632Ht × A634Ht) × MO17 |

TYPE 3: WIDELY MODIFIED SINGLE CROSS OR 3-WAY CROSS

| Type | Pedigree |
|---|---|
| Type 3-A | (A635Ht × B14AHt) × MO17 |
| Type 3-B | (H93 × H84) × D71-4 |

Using these types, experiments were conducted in 1977 on plots located at West Liberty, Iowa. Similar experiments were conducted also in 1978 and 1979 at both West Liberty, Iowa and Illinois City, Ill. For purposes of analysis, each location and year have been equated to an "Environment." Environment 1 is the location at West Liberty, Iowa in 1977. Environments 2 and 3 are the locations at West Liberty, Iowa and Illinois City, Ill., respectively, in 1978. Environments 4 and 5 are the locations at West Liberty, Iowa, and Illinois City, Ill., respectively, in 1979. Environment 1 had one or two replications; Environment 2 had two or three replications; Environment 3 had three replications; Environment 4 had two or three replications; and Environment 5 had one entry. The yields of the Environments are shown in Table 2. Seed produced from the top ear is referred to as the "Control," and seed produced by my novel method is referred to as "Lower Ear".

TABLE 2

YIELDS IN DIFFERENT ENVIRONMENTS

| TYPE | ENVIRONMENTS | | | | |
|---|---|---|---|---|---|
| | 1 | 2 | 3 | 4 | 5 |
| | Mean Yield Bu/Acre | | | | |
| 1-A Control | 144 | 126 | 227 | 146 | 163 |
| 1-A Lower Ear | 153 | 122 | 244 | 183 | 213 |
| 1-B Control | — | — | — | 151 | — |
| 1-B Lower Ear | — | — | — | 174 | — |
| 1-C Control | 101 | 60 | — | — | — |
| 1-C Lower Ear | 188 | 125 | — | — | — |
| 2-A Control | 97 | 74 | 189 | 111 | 139 |
| 2-A Lower Ear | 138 | 178 | 228 | 138 | 157 |
| 2-B Control | 131 | 103 | 180 | 152 | 166 |
| 2-B Lower Ear | 133 | 115 | 203 | 148 | 169 |
| 3-A Control | 157 | 104 | 161 | 129 | 155 |
| 3-A Lower Ear | 112 | 111 | 165 | 170 | 172 |
| 3-B Control | — | — | — | 133 | — |
| 3-B Lower Ear | — | — | — | 176 | — |

Each Environment of Table 2 was hand planted at 24,500 average plants per acre, not thinned, hand harvested, weighed, moisture tested, and converted to number of bushels of No. 2 corn per acre. In all five Environments 30 inch rows, 17 feet, 5 inches long were used. In Environment 1, a single row of Lower Ear produced $F_1$ seed was planted next to a Control $F_1$ row. In all other Environments two rows of Lower Ear $F_1$ seed were planted next to two Control $F_1$ rows.

The yield increases for the $F_1$ plants produced from my novel method when compared with identical pedigrees produced by conventional fertilization of the top ear have been up to 25% and are shown in Table 3.

TABLE 3

YIELD DIFFERENCES

| | Mean Bushels/Acre | | |
|---|---|---|---|
| TYPES | CONTROL | LOWER EAR | PERCENT INCREASE |
| Type 1 | 140 | 175 | 25% |
| Type 2 | 134 | 161 | 20% |
| Type 3 | 140 | 151 | 8% |

Pure-line single crosses were increased 25% in yield, closely-related single crosses by 20%, and widely-modified single crosses or three-way crosses by 8%.

In my research, I noted that grow-outs of Lower Ears on inbreds during 1977 yielded less than their control counterpart. Therefore, my method is not useful in producing increased yields with inbreds, only in producing increases with hybrid crosses.

The novel method of breeding and producing yellow dent seed corn using the principles of the invention are fully applicable to single crosses, threeway crosses, and double crosses, and it will be obvious to those skilled in the art that the principles of the invention are fully applicable to all pedigrees of yellow dent corn regardless of genetic background. It is my intention that the techniques of my invention encompass all hybrid crosses and not be limited except as defined in the following claims.

I claim:

1. A method of producing yellow dent hybrid seed corn comprising:
    planting a selected ear parent strain of a corn plant,
    allowing said corn plant to grow until the top ear shoot emerges from a leaf sheath of the corn plant,
    preventing fertilization of the top ear shoot,
    allowing the silks to emerge from an ear shoot below the top ear shoot,
    causing pollination of the lower ear shoot from an unrelated pollen parent plant, and
    harvesting the seed corn produced from fertilization of the lower ear shoot, whereby the seed from the lower ear shoot will produce a higher yield the next generation than seed from the top ear shoot.

2. The method of claim 1 in which fertilization of the top ear shoot is prevented by causing abortion of that shoot before silks emerge from it.

3. The method of claim 2 in which abortion of the top ear shoot is accomplished by physically removing that shoot before the silks emerge from it.

4. The method defined in claims 1, 2 or 3 in which the resultant hybrid is a pure-line single cross.

5. The method defined in claims 1, 2, or 3 in which the resultant hybrid is a closely related sister-line single cross.

6. The method defined in claims 1, 2 or 3 in which the resultant hybrid is a widely modified single cross or three-way cross.

7. The method defined in claims 1, 2 or 3 in which the resultant hybrid is a double-cross.

* * * * *